United States Patent [19]

Quadro

[11] 4,447,419

[45] May 8, 1984

[54] THIAZOLE DERIVATIVE, AND PHARMACEUTICAL COMPOSITIONS CONTAINING IT

[75] Inventor: Giuseppe Quadro, Milan, Italy

[73] Assignee: Ausonia Farmaceutici s.r.l., Rome, Italy

[21] Appl. No.: 438,283

[22] Filed: Nov. 1, 1982

[30] Foreign Application Priority Data

Nov. 5, 1981 [IT] Italy ............................... 24866 A/81

[51] Int. Cl.$^3$ ..................... C07C 103/52; A61K 37/02; A61K 37/64
[52] U.S. Cl. .................................... 424/177; 424/270; 260/112.5 R; 548/201
[58] Field of Search ................. 548/201; 260/112.5 R; 424/177, 270

[56] References Cited

U.S. PATENT DOCUMENTS

4,374,249  2/1983  Moran ................................ 548/201

FOREIGN PATENT DOCUMENTS

3012140  10/1980  Fed. Rep. of Germany ... 260/112.5 R

OTHER PUBLICATIONS

McOmie, Protective Groups in Org. Chem. pp. 286–295 (1973).
Greene, Protective Groups in Org. Syn. pp. 208–210 (1981).

*Primary Examiner*—Robert Gerstl
*Attorney, Agent, or Firm*—Walter H. Schneider

[57] ABSTRACT

The present invention relates to the 3-[N-(2-mercapto-propionyl-amino-acetyl)]-tetrahydro-thiazolyl-4-carboxylic acid and pharmaceutical compositions containing it, endowed with a marked inhibitory activity of the angiotensin converting enzyme (ACE).

2 Claims, No Drawings

THIAZOLE DERIVATIVE, AND PHARMACEUTICAL COMPOSITIONS CONTAINING IT

The present invention relates to a novel compound, namely 3-[N-(2-mercapto-propionyl-amino-acetyl)]-tetrahydro-thiazolyl-4-carboxylic acid having formula

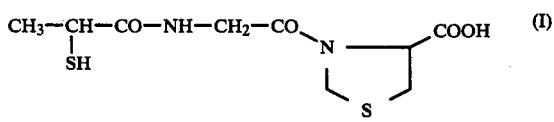

The compound of the invention is characterized by a marked inhibitory activity of the angiotensin converting enzyme as well as by a considerable hepatoprotective activity, a clearly positive effect on liver regeneration and a high bronchosecretolytic activity. The compound (I) will be henceforth defined, for sake of shortness, also with the abbreviation MR 729.

The process for the preparation of the compound of the invention is characterized by reacting an activated derivative of benzoylmercaptopropionylglycine, such as, for instance, a halide, a symmetric or, preferably, mixed anhydride with a metal salt of 4-carboxy-thiazolidine, and subsequently cleaving the benzoyl group of the so obtained intermediate, according to the following scheme:

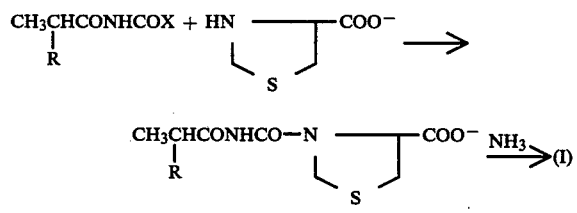

Wherein R=$C_6H_5$—CO—S—, X is halogen, preferably chlorine, or a residue forming a symmetric or mixed anhydride with the rest of the molecule. Preferably, X is the residue O—CO—$OC_2H_5$.

The reaction temperatures range between −20° and +10° C. As regards molar ratios, a slight excess of salt of 4-carboxy-thiazolidine is used. The salt of 4-carboxy-thiazolidine may be the alkaline metal or alkaline-earth metal salt and may also be prepared "in situ".

The following example illustrates this invention, without limiting its scope in any way.

EXAMPLE (a)

3-[N-(2-benzoylmercaptopropionyl-aminoacetyl)]-tetrahydrothiazolyl-4-carboxylic acid A solution of 6 g of ethyl chloroformiate (0.0552 moles) in tetrahydrofuran (20 ml) is added dropwise under magnetic stirring, keeping the temperature between −10° and 0° C., to a solution of 13.4 g (0.056 moles) of 2-benzoylmercapto-propionyl-glycine and 6 g (0.0594 moles) of triethylamine in tetrahydrofuran (70 ml).

After the temperature has raised to −5° C., 8 g (0.06 moles) of 4-carboxy-thiazolidine and 3.4 g (0.06 moles) of KOH dissolved in water (40 ml) are added. The reaction mixture is then stirred for 24 hours at room temperature.

After solvent evaporation, the reaction mixture is heated with water (acidic reaction) and extracted with dichloromethane. The organic phase is dried on $Na_2SO_4$ and the solvent evaporated under reduced pressure to give 20 g of crude product.

(b)

3-[N-(2-mercapto-propionyl-amino-acetyl)]-tetrahydrothiazolyl-4-carboxylic acid

The crude product is treated with methanol (150 ml) and concentrated $NH_3$ (60 ml); the resulting mixture is then refluxed for 1 hour.

The solvent is evaporated under reduced pressure and the remaining water is removed from the benzamide by filtration. The aqueous phases are acidified with $H_2SO_4$ and extracted with $CH_2Cl_2$ (∼50 ml). The organic phase is left to stand at 0° C. for 1 hour; 4.5 g of precipitate are obtained, which, after crystallization from tetrahydrofuran/ethyl ether (50:50 ml), yield 3.9 g of pure product melting at 160°–163° C.

Aspect: white crystalline powder

I.R. spectrum: 1740 $cm^{-1}$; 1625 $cm^{-1}$ (broad band)

$H^1$-N.M.R. spectrum: (detected in hexadeuterodimethylsulfoxide, inner standard TMS; chemical shifts are expressed in δ): 1.35(d, 3H, $CH_3$—); 4.7(q, 1H, $CH_3$—$\underline{CH}$); 7.3–8.4 (m, 3H, mobile).

The biological and pharmacological characteristics of the compound of the invention are reported hereinafter.

Acute toxicity

The toxicity of MR 729 after single administration has been studied in mice, by injecting the product at different doses by the intraperitoneal route. It has been determined a $LD_{50}$ value of 395 mg/kg, with 95% confidence limits of 307–478.

Pharmacological properties

Inhibitory activity of angiotensin converting enzyme (ACE)

It is known that substances able to inhibit the angiotensin converting enzyme (ACE) have potential therapeutic applications in the treatment of hypertension.

The plasma ACE has been determined by the method of Summary et al. (Clin. Sci. 50, 321, 1976) using histidyl-glycyl-histidine as a substrate.

Tests have been carried out with 20 ml of normal human serum.

A 0.1 M aqueous solution of MR 729 has been used. The data reported hereinafter show that MR 729 exhibits a high "in vitro" inhibitory activity of ACE, with an $ID_{50}$ of 60 μMol per mol of serum.

| Drug | | % Enzymatic activity |
|---|---|---|
| — | 30 nmol/10 min/20 μl | 100 |
| MR 729 20 μl | 9 nmol/10 min/20 μl | 30 |
| MR 729 50 μl | 7 nmol/10 min/20 μl | 23 |
| MR 729 100 μl | 3 nmol/10 min/20 μl | 10 |

Intoxication by $CCl_4$

The study has been carried out on 12 hours fasting rats; MR 729 was administered by oral route at different doses 2 hours before carbon tetrachloride. The animals were sacrificed after 20 hours and the liver was removed for the determination of liver lipids.

It has been shown that MR 729 is able to inhibit, in a dose-dependent way, the lipid infiltration experimentally induced by CCl4.

Intoxication by ethionine

Also ethionine administration causes in the rat hepatic damages with respect to hepatocytes, occurring as a massive lipidic infiltration. The daily oral administration of MR 729, during the 8 days preceding ethionine treatment, proved to be effective in antagonizing, with a dose-related intensity, the establishment of this pathology.

Intoxication by α-naphtyl-isothiocyanate

The hepatic damage caused by 8 days prolonged administration of α-naphtyl-isothiocyanate causes in the rate impairments in respect of cellular proliferation and hypertrophy of periportal spaces. The contemporary oral treatment with MR 729 inhibits the development of such pathology.

The histological examinations have in fact evidenced that the structure of biliary ducts in the treated animals was practically unchanged and that there were not any noticeable parenchimal alterations.

Effect on liver regeneration

This study aimed to evidence whether MR 729 could affect the liver regeneration in partially hepathectomized rats.

The animals have been treated with the product under study just after their operation; the regeneration degree has been assessed after 4 days. It has been shown that MR 729 acts in a positive way on the regeneration process, without however a clear dose-effect relationship.

Prolongation of barbiturates induced sleep

Since the length of barbiturates induced sleep can be considered directly related to the metabolism rate of these drugs by the liver, it seemed appropiate to assess the influence of MR 729 on the time of hexobarbital induced sleep in rats intoxicated by carbon tetrachloride.

MR 729 has been administered by oral route for 4 consecutive days, at different doses; the animals were then treated with CCl4 and, after 48 hours, with hexobarbital. It has been observed that the preventive administration of MR 729 inhibits the remarkable prolongation of sleeping time induced by pre-treatment with CCl4 alone.

This inhibition is dose-dependent; at highest doses, sleeping times are, in fact, practically within normal limits.

"In vitro" mucolytic effect

It has been followed the method described by Scheffner (Ann. N.Y. Acad. Sci. 106, 298, 1963) using as a substrate pig's lyophilized gastric mucine. In these experimental conditions MR 729 showed to possess a dose-dependent mucolytic effect, decreasing the viscosity of 17-35% according to the considered dose. This activity proved to be 35-50% higher, according to the doses, than that showed by equiponderant doses of N-acetyl-S-cysteine in the same experimental conditions.

"In vivo" mucolytic effect

The effect of MR 729 on bronchial secretion has been studied in the rat with the method of sodium fluorescein described by Mawatari (Kagoshima Daigakeu Igakeu Zasshi, 27, 561, 1976).

The product under study has been administered by intraperitoneal route 5 minutes before the solution of sodium fluoroscein, whose amount in the bronchial secretion has been determined after 30 minutes. According to the results obtained, it can be said that MR 729 has a remarkable bronchosecretolytic effect: it exerts, in fact, at the dose of 250 mg/kg, a fivefold higher activity than that shown, in the same experimental conditions, by carboxymethylcysteine at the dose of 500 mg/kg i.p.

Effect on glutathione-peroxidase

It is known that the peroxidation of endogenous unsaturated acids in the mithochondrial and microsomial membranes represents one of the more precocious and important manifestation of liver intoxication.

This peroxidation phenomenon can be induced both in vitro, by oxidizing substances such as oxidized glutathione, and in vivo by agents such as CCl4 or ionizing radiations.

On the ground of these considerations and considering the above described pharmacological results, it has been assessed the efficacy of MR 729 in inhibiting in vitro the rat hepatic glutathione-peroxidase (GSH-P).

It has been used the system glutathione/NADPH/GSH-reductase/cumene hydroperoxide. It was shown that MR 729 inhibits of about 63% the GSH-P, at a concentration of 0.025 mM. The administration of MR 729 allows therefore a saving of endogenous glutathione and a consequent decrease of free peroxides. Compound MR 729 can be administered by oral, parenteral, rectal, aerosolic route in various forms. The compositions below are described as an example:

100-400 mg capsules/pills/tablets of MR 729.

100-500 mg vials (for parenteral and aerosolic use) of MR 729.

1%-2%-3% syrups in MR 729.

200-800 mg suppositories of MR 729.

1%-2%-3% monodose sachets of MR 729.

I claim:

1. 3-[N-(2-mercapto-propionylamino-acetyl)]-tetrahydro-thiazolyl-4-carboxylic acid, having formula (I)

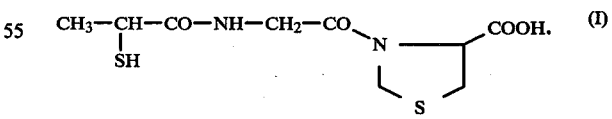

2. Pharmaceutical compositions endowed with antihypertensive, hepatoprotective and bronchosecretolytic activities, which can be administered by oral, parenteral, aerosolic route, characterized in that they contain compound (I) as the active agent.